United States Patent
Suehling et al.

(10) Patent No.: US 10,779,787 B2
(45) Date of Patent: Sep. 22, 2020

(54) METHOD FOR ANALYZING IMAGE DATA FROM A PATIENT AFTER A MINIMALLY INVASIVE INTERVENTION, ANALYSIS APPARATUS, COMPUTER PROGRAM AND ELECTRONICALLY READABLE DATA STORAGE MEDIUM

(71) Applicant: Siemens Healthcare GmbH, Erlangen (DE)

(72) Inventors: Michael Suehling, Erlangen (DE); Thomas Flohr, Uehlfeld (DE); Stefan Reichelt, Bamberg (DE)

(73) Assignee: Siemens Healthcare GmbH, Erlangen (DE)

( * ) Notice: Subject to any disclaimer, the term of this patent is extended or adjusted under 35 U.S.C. 154(b) by 118 days.

(21) Appl. No.: 16/059,197

(22) Filed: Aug. 9, 2018

(65) Prior Publication Data

US 2019/0046148 A1 Feb. 14, 2019

(30) Foreign Application Priority Data

Aug. 11, 2017 (EP) ..................................... 17185866

(51) Int. Cl.
*G06K 9/36* (2006.01)
*A61B 6/00* (2006.01)
(Continued)

(52) U.S. Cl.
CPC ............. *A61B 6/5241* (2013.01); *G06N 3/08* (2013.01); *G06T 7/0012* (2013.01); *G06T 7/11* (2017.01);
(Continued)

(58) Field of Classification Search
CPC .... A61B 5/00; A61B 6/00; A61B 6/03; A61B 6/032; A61B 6/5217; A61B 5/7267;
(Continued)

(56) References Cited

U.S. PATENT DOCUMENTS 10,467,761 B2* 11/2019 Weistrand ............. G06T 7/0012
2004/0236225 A1* 11/2004 Murphy ................. A61B 5/015
600/473

(Continued)

FOREIGN PATENT DOCUMENTS

DE 102014212089 A1 7/2015
EP 3441936 A1 * 2/2019 ............... G06T 7/40
(Continued)

OTHER PUBLICATIONS

Maday, Peter et al. "Imaging as a Surrogate for the Early Prediction and Assessment of Treatment Response through the Analysis of 4-D Texture Ensembles (ISEPARATE)" Network and Parallel Computing; [Lecture Notes in Computer Science; Lect.Notes Computer], Springer International Publishing, Cham, Bd. 6533 Chap.16, Nr. 558, pp. 164-173, XP047442062, ISSN: 0302-9743; ISBN: 978-3-642-01969-2; 2010.

(Continued)

*Primary Examiner* — Mahendra R Patel
(74) *Attorney, Agent, or Firm* — Harness, Dickey & Pierce, P.L.C.

(57) ABSTRACT

A method is disclosed for analyzing image data from a patient after a minimally invasive intervention on a lesion, in particular after a tumor ablation on a tumor, wherein a pre-intervention image dataset showing the lesion and an intra- and/or post-intervention, second image dataset showing the intervention region are analyzed. In at least one embodiment of the method, the method includes deriving attribute data describing attributes of the image data from the image datasets at least in part automatically, the attribute data being usable as input data to an artificial intelligence analysis algorithm trained using training data from other patients, and the training data being associated with a ground truth. The method further includes determining, from the attribute data, change information that describes the change (Continued)

in the lesion and/or in the intervention region as a result of the intervention.

20 Claims, 1 Drawing Sheet

(51) Int. Cl.
    *G06T 7/00*     (2017.01)
    *G06T 7/11*     (2017.01)
    *G06T 7/70*     (2017.01)
    *G06N 3/08*     (2006.01)
    *G06T 7/40*     (2017.01)

(52) U.S. Cl.
    CPC .................. *G06T 7/40* (2013.01); *G06T 7/70* (2017.01); *G06K 2209/05* (2013.01); *G06T 2207/20081* (2013.01); *G06T 2207/30096* (2013.01)

(58) Field of Classification Search
    CPC ....... A61B 6/5229; A61B 5/7264; G06T 7/42; G06T 7/0016; G06T 2207/10072; G06T 2207/10136; G06T 2207/20012; G06T 7/0012; G06T 2207/20081; G06K 9/6256; G06K 9/6259; G06K 9/6214; G06K 9/624; H04J 3/06; H04N 5/3658; G06N 3/08
    USPC ......... 382/128, 131, 305, 284; 600/408, 437
    See application file for complete search history.

(56) References Cited

U.S. PATENT DOCUMENTS

| | | | | |
|---|---|---|---|---|
| 2005/0041843 A1* | 2/2005 | Sawyer | ............... | A61N 5/1049 382/128 |
| 2006/0018524 A1* | 1/2006 | Suzuki | ............... | G06K 9/6292 382/128 |
| 2006/0269111 A1* | 11/2006 | Stoecker | ............... | G06T 7/0012 382/128 |
| 2007/0167784 A1* | 7/2007 | Shekhar | ............... | A61B 6/032 600/443 |
| 2007/0201735 A1* | 8/2007 | Gundel | ............... | G06T 7/0012 382/128 |
| 2007/0238992 A1* | 10/2007 | Donofrio | ............... | A61B 5/076 600/437 |
| 2008/0292194 A1* | 11/2008 | Schmidt | ............... | G06T 7/0012 382/217 |
| 2010/0111396 A1* | 5/2010 | Boucheron | ............ | G06K 9/6231 382/133 |
| 2012/0071758 A1* | 3/2012 | Lachaine | ............ | A61N 5/1049 600/439 |
| 2012/0189176 A1* | 7/2012 | Giger | ................... | G06K 9/6253 382/128 |
| 2013/0272593 A1* | 10/2013 | Lee | ......................... | A61N 5/103 382/131 |
| 2013/0329973 A1* | 12/2013 | Cao | ...................... | A61B 5/0033 382/128 |
| 2014/0037161 A1* | 2/2014 | Rucker | ................. | A61B 34/20 382/128 |
| 2015/0087957 A1* | 3/2015 | Liu | ....................... | G06K 9/6214 600/408 |
| 2015/0196265 A1* | 7/2015 | Suzuki | ................. | G06K 9/6262 378/37 |
| 2015/0282714 A1* | 10/2015 | Mueller | ................ | A61B 90/30 348/37 |
| 2019/0015080 A1* | 1/2019 | Kreuzer | ............... | A61B 8/565 |
| 2019/0231249 A1* | 8/2019 | Dascalu | ............... | A61B 5/0095 |

FOREIGN PATENT DOCUMENTS

| | | | | |
|---|---|---|---|---|
| KR | 20150112625 A | * | 10/2015 | |
| KR | 101600323 B1 | * | 3/2016 | |
| WO | WO-2015048103 A1 | * | 4/2015 | ............. A61B 6/032 |
| WO | WO-2016039763 A1 | * | 3/2016 | ........... G06T 3/0068 |

OTHER PUBLICATIONS

Extended European Search Report #17185866.5 dated Feb. 8, 2018.

* cited by examiner

METHOD FOR ANALYZING IMAGE DATA FROM A PATIENT AFTER A MINIMALLY INVASIVE INTERVENTION, ANALYSIS APPARATUS, COMPUTER PROGRAM AND ELECTRONICALLY READABLE DATA STORAGE MEDIUM

PRIORITY STATEMENT

The present application hereby claims priority under 35 U.S.C. § 119 to European patent application number EP17185866.5 filed Aug. 11, 2017, the entire contents of which are hereby incorporated herein by reference.

FIELD

At least one embodiment of the invention generally relates to a method for analyzing image data from a patient after a minimally invasive intervention on a lesion, in particular after a tumor ablation on a tumor, wherein a pre-intervention image dataset showing the lesion and an intra- and/or post-intervention, second image dataset showing the intervention region are analyzed. At least one embodiment of the invention also generally relates to an analysis apparatus, to a computer program and/or to an electronically readable data storage medium.

BACKGROUND

To date, numerous minimally invasive intervention techniques for treating lesions, in particular tumors, inside a patient have already been proposed. These techniques usually involve guiding a minimally invasive medical instrument, for instance a treatment needle and/or a catheter, to the lesion, where the intervention for performing the treatment is then accordingly carried out. An example of this is the ablative treatment of tumors (tumor ablation), in which both primary tumors and metastases can be treated in basically all the regions of the body. Tumor ablation is a technique that aims to destroy cells and tissues in a controlled manner, in particular by thermal treatment (heating or cooling). Frequently used treatment techniques include percutaneous radio frequency ablation (RFA), microwave ablation (MWA), and cryoablation.

Minimally invasive interventions, in particular tumor ablations, are also often performed under image monitoring. This involves using an image acquisition apparatus, for instance a radiography apparatus, to acquire image data of the intervention region and of the lesion under treatment. In particular, computed tomography (CT) has also been proposed as a navigation tool in minimally invasive interventions.

In addition to using image datasets produced during and/or at the end of the minimally invasive intervention (intra- and/or post-intervention image data), the minimally invasive intervention often also uses pre-intervention image data as a basis, for instance three-dimensional planning datasets, which data shows the lesion sufficiently clearly and can be used as overlay images in image monitoring of the minimally invasive intervention. Numerous different descriptions of suitable techniques for assisting by image monitoring a person performing an intervention are known.

The problem with a minimally invasive intervention of this type is that the success or failure of the minimally invasive intervention at present cannot be assessed reliably on the basis of the acquired image data and/or other information. In clinical practice, a person performing the intervention usually assesses the result of the treatment visually and qualitatively on the basis of image data that was acquired during or immediately after the minimally invasive intervention, i.e. including intra- and/or post-intervention image data. Since the assessment is performed by a person looking at the image data, the assessment result can be described as subjective and person-dependent.

In the image datasets, for instance CT scans, varying visual impressions are gained, for example borders of necrotic tissue, cavitations or "ground glass opacities" (GGO) around the lesion. A tumor diameter may decrease or not change during the intervention, depending on the type of tumor. The result is situations in which the treatment is "overdone", i.e. too intense a treatment is performed, which constitutes an unnecessary risk or an unnecessary complication for the patient. On the other hand, when the treatment is not sufficient, parts of the tumor that are left can result in the disease progressing, which likewise poses a risk for the patient.

SUMMARY

The inventors have discovered that such systems does not allow a reliable assessment of the treatment success to be made until significantly after the minimally invasive intervention has been performed, for instance on the basis of follow-up image acquisitions. They have recognized that the problem here is that effective quickly-taken corrective actions, in particular further ablative interventions, are no longer possible on this time scale.

Therefore, at least one embodiment of the invention provides an improved assessment of the treatment success of a minimally invasive intervention closer in time to the intervention, in particular during and/or immediately after the intervention.

In a method of at least one embodiment of the invention, attribute data describing attributes of the image data is derived from the image datasets at least in part automatically, which attribute data is provided as input data to an artificial intelligence analysis algorithm that is trained using training data from other patients, which training data is associated with a ground truth, and that determines from the attribute data, change information that describes the change in the lesion and/or in the intervention region as a result of the intervention.

In a method of at least one embodiment of the invention, using image data from a patient after a minimally invasive intervention on a lesion, a pre-intervention image dataset showing the lesion and at least one of an intra-intervention and post-intervention, and a second image dataset showing an intervention region, the method comprises:

deriving attribute data describing attributes of the image data from the pre-intervention image dataset and the second image dataset, at least in part automatically, the attribute data being usable as input data to an artificial intelligence analysis algorithm, trained using training data from other patients, the training data being associated with a ground truth; and determining, from the attribute data derived, change information describing a change in at least one of the lesion and the intervention region as a result of the intervention.

At least one further embodiment of the invention is directed to an analysis apparatus comprising at least one processor that is designed to perform the method according to at least one embodiment of the invention. All the statements relating to the method according to embodiments of the invention can also be applied analogously to the analysis apparatus according to embodiments of the invention, and therefore the advantages already described can also be achieved by the apparatus.

The analysis apparatus, in at least one embodiment, can comprise for this purpose in particular a training unit, an attribute-data determination unit and an analysis unit. Additional units may be an output unit, a registration unit, various subunits, and the like. The analysis apparatus can comprise a communications interface to an image archiving system (PACS) and/or to an image acquisition apparatus, in particular an image acquisition apparatus used for image monitoring of the intervention, and/or to an information system, for instance a hospital information system (HIS) and/or a radiology information system (RIS), in order to retrieve at least some image data and/or information to be used to determine attribute data or to be used as additional input data.

At least one additional embodiment of the invention is directed to a computer program, which can be loaded directly into a memory of an analysis apparatus, and comprises program segments to perform the steps of at least one embodiment of a method described herein when the computer program is executed in the analysis apparatus.

At least one additional embodiment of the invention is directed to a non-transitory electronically readable data storage medium storing a computer program, which therefore comprises electronically readable control information stored thereon that comprises at least one computer program and is designed such that it performs at least one embodiment of a method described herein when the data storage medium is used in an analysis apparatus. The data storage medium may be a non-transient data storage medium, for instance a CD-ROM.

BRIEF DESCRIPTION OF THE DRAWINGS

Further advantages and details of the present invention are presented in the example embodiments described below and with reference to the drawings, in which.

DETAILED DESCRIPTION OF THE EXAMPLE EMBODIMENTS

Figure 1:
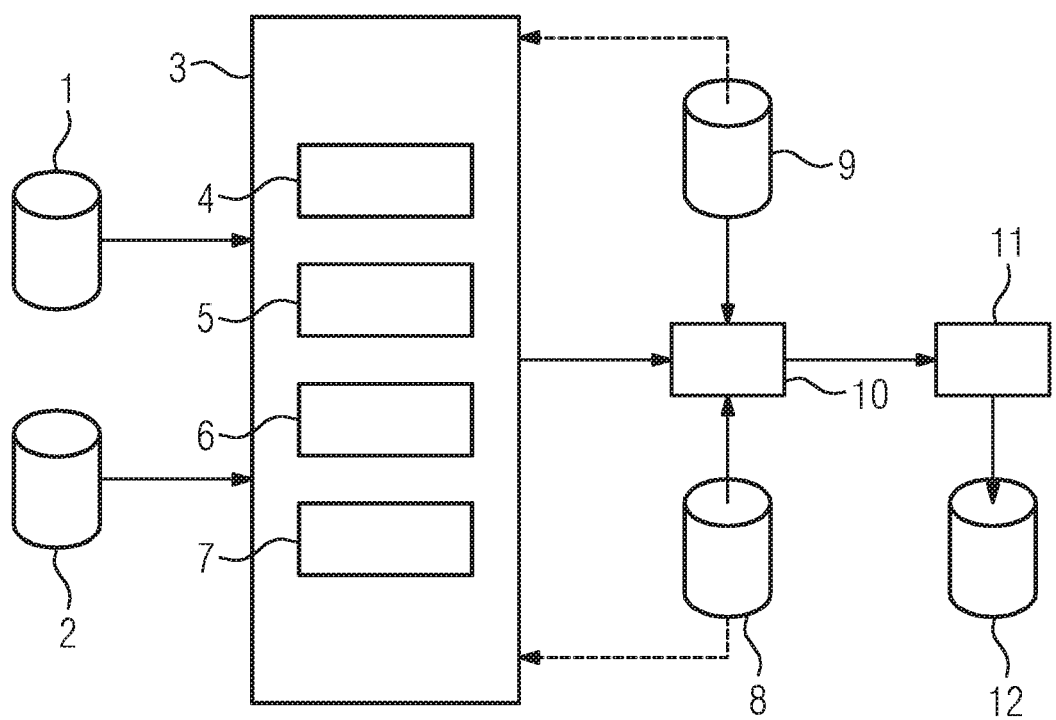
FIG. 1 is a relationship diagram of an example embodiment of the method according to the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In a method of at least one embodiment of the invention, attribute data describing attributes of the image data is derived from the image datasets at least in part automatically, which attribute data is provided as input data to an artificial intelligence analysis algorithm that is trained using training data from other patients, which training data is associated with a ground truth, and that determines from the attribute data, change information that describes the change in the lesion and/or in the intervention region as a result of the intervention.

Thus, a data-driven approach is proposed according to at least one embodiment of the invention in order to facilitate an objective assessment of the treatment result early during and/or after the intervention in order to allow early and optimum patient management. The change information is used to provide objective evaluation information which describes the change that has taken place in the intervention region or specifically at the lesion and which forms an excellent basis for an assessment and hence a consequent diagnosis, which a person performing the treatment must make. It has been found here that artificial intelligence methods or machine learning methods can be applied particularly advantageously in this field. These procedures manage without explicit physical modeling, for instance without physical models that describe the heat transfer on the basis of differential equations. Subjective and/or possibly false assumptions can largely be eliminated by a purely data-driven approach, in which in particular the training algorithm used in training the analysis algorithm deduces by itself the physical relationships and correlations.

Various suitable specific artificial intelligence analysis algorithms can be used in this approach. A neural network and/or a random forest algorithm can preferably be used as the analysis algorithm.

A particularly advantageous embodiment of the present invention provides that at least some of the attribute data and/or attributes of the analysis algorithm, which are to be used as input data, are defined by a training algorithm, in particular a deep-learning algorithm, that trains the analysis algorithm. If deep-learning techniques are used, the training algorithm is therefore provided with the image data directly so that it can learn the physical relationships present in this data, and can select the attributes of the image data that best describe these relationships or correlations just like the analysis algorithm can be configured to be suitably adapted to the attributes. It is conceivable in particular that the training algorithm itself defines at least some of the suitable attributes to be derived from the image data. Such attributes can also be referred to as "deep-learning attributes".

Alternatively or additionally, it is also conceivable, in at least one embodiment of the present invention, that at least some of the attribute data to be used as input data is selected from a predetermined set of candidate data describing candidate attributes. If candidate attributes that are expected to have a strong association with the change information are already known, for example from studies, scientific analyses, and the like, then they can be supplied accordingly to a training algorithm, in particular also to the deep-learning training algorithm, something which may possibly simplify the training process overall if it is already possible here to find suitable input data within the candidate data.

A particularly advantageous development of at least one embodiment of the present invention provides that acquisition parameters associated with the image datasets and used for acquiring image data of the image datasets are used in addition as input data of the analysis algorithm and/or for determining the attribute data. It is often relevant in image interpretation, how the image concerned was produced, for instance what intensity is used to render contours in an X-ray image, what contrasts are represented by the image data for instance in a magnetic resonance image, and the like. This can affect both the specific determination of the attribute data for this image data and the work of the analysis algorithm itself, because it is then possible to cover the total bandwidth of possible acquisition parameters for the image data and to take this into account in the relationships described by the analysis algorithm. General acquisition parameters, for example, relate to the acquisition time, contrast agent properties, the imaged region of the patient, the image acquisition modality or image acquisition equipment used, acquisition geometry parameters, and the like. In particular the dose and/or the energy spectrum of the X-rays should be mentioned here specifically for radiographic data.

It is also particularly advantageous if at least some of the image data comprises multi-energy radiographic data containing associated energy-spectrum information. Multi-energy radiography, in particular dual-energy radiography, provides a large amount of additional information because of the absorption properties of different materials, which properties are partially dependent on the radiation energy distribution, and this information can be used particularly advantageously as part of both machine learning and applying the analysis algorithm in its entirety. Spectral CT must be mentioned here in particular. It is possible to take into account and use this wide variety of information to the greatest extent possible by the embedding in a data-driven system using artificial intelligence.

In the context of at least one embodiment of the present invention, a wide variety of attribute data can be used and taken into account. A group of attribute data that has proved suitable comprises identification and position information relating to the lesion and/or to the anatomical structures surrounding the lesion, in particular as annotated regions, and/or instrument information relating to an instrument that is used and is visible in the image data. Such attribute data can be derived in part or even in full automatically from the image data by using known modern algorithms.

Identification and position information relating to anatomical structures define, for instance, the nature and extent of these anatomical structures which surround the target lesion, preferably for all the times covered by image data. For example in this case, the position and extent of organs such as the liver or lungs can be described, wherein a particularly advantageous embodiment provides that for thermal tumor ablation and/or other thermal treatments, thermal conduction information describing thermal conduction paths is included as specific attribute data in thermal treatments. It is thereby possible to describe blood vessels and/or airways, which can act as heat sinks during the minimally invasive intervention.

In this context, attribute data can optionally also comprise biophysical tissue properties, which are associated with the identified anatomical structures and which likewise can be included in the total attribute dataset. Similar observations relate also to the lesion, in which case it is particularly advantageous if all the times covered by image data are taken into account, i.e. the identification and extent of the lesion as target region are known for all these times. Again in this case, algorithms that can determine this information automatically have already been proposed.

Determining the attribute data can also comprise instrument detection if the instrument can be seen in the image data, and instrument localization, resulting in geometry data and the position of instruments and/or other devices inside the image data. Geometry data relating to the instrument can be derived advantageously here from intervention procedure data describing the intervention, for instance from a CAD model of the instrument.

Another group of possible attribute data comprises attribute data describing shape and texture attributes of the image data, which attribute data can likewise be used in the context of the present invention. It can be provided here that attributes described by the attribute data include at least one element from the following group: characteristic value, in particular mean values, entropy and central moments, derived from at least one intensity histogram; shape attributes, for instance size, density, eccentricity, sphericity and/or compactness; image texture attributes such as intra-tumor heterogeneity, Gabor jets and results from LoG, edge filters and/or wavelets; image voxel associations, for instance the maximum length of identical image values, information on gray levels in the surrounding area of an image element and/or dependence matrices; fractal properties; and attributes from spectral CT, for instance an iodine map and/or virtual non-contrast images.

It can be provided, in a particularly advantageous development of at least one embodiment of the present invention, that patient information and/or diagnostic information relating to the patient and/or intervention information describing the intervention is used in addition as input data of the analysis algorithm and/or for determining the attribute data. Hence the analysis can be significantly improved further by additionally taking into account non-image information.

Such non-image information can include as intervention information, in particular, the type of intervention (for instance RF ablation, microwave ablation or cryoablation), the intervention times (for instance start and end points of the use of an instrument), the energy that has been introduced, measured temperatures (for instance by additionally inserted temperature measuring devices), instrument geometries and attributes, and the like, and/or as patient data, for example, information such as blood-clotting attributes of the patient, administered medication, gender of the patient, age of the patient, and/or size of the patient.

Classification information allowing a temporal and/or spatial classification can advantageously be assigned to each item of attribute data and/or additional input data. At the latest when combining the input data, for instance as an input data vector, for the analysis algorithm it is advantageous to assign, i.e. in particular to add, to at least some of the individual attributes and/or, if applicable, to the additional information, where possible temporal and/or spatial classification information, so that the analysis algorithm can also take this classification information into account. For example, individual items of attribute data on the lesion can be assigned the times at which was acquired the image data from which this attribute data was derived, and the like. In other words it is thereby possible to perform spatial/temporal mapping of the attributes and, if applicable, of the additional information, over the times at which image data and, if applicable, additional information exist.

It can be provided in general, in the context of at least one embodiment of the present invention, that the change information and/or output information derived therefrom is output to a user. An advantageous embodiment in this context provides that an analysis representation to be presented as an overlay on at least one item of the image data is generated from the change information and analyzed. It is thereby possible to show important changes in addition to the image data in order to make this more comprehensible.

A particularly advantageous development of at least one embodiment of the invention can also provide, however, that a visual reproduction of attribute data to be presented as an overlay on at least some of the image data is generated and output, in a corresponding overlay, as the analysis representation or additional analysis representation. This allows essential image attributes to be visualized in the image data itself, so that ultimately a visual demonstration of the result described by the change information can be output to a user. It is conceivable in particular that the user himself can mentally check the result of the analysis algorithm again or at least incorporate the analysis representation in his final assessment of the intervention success.

In a particularly preferred embodiment, it can be provided that when a ground truth exists for a patient for whom change information has been determined, image data from the patient and the ground truth, and in particular divergence information, can be used as training data for further training of the algorithm. Thus as soon as it is known for a patient whether or not the intervention was successful and/or what change in the lesion has occurred, this ground truth can be used to improve further the analysis algorithm and hence to implement a constantly learning system, the analysis tools of which become increasingly substantiated and reliable.

At least one embodiment of the present invention can provide that the analysis algorithm is trained by a central back-end facility that uses training data from a plurality of medical infrastructure facilities. The results and/or ground truths and image data from a very wide range of medical infrastructure facilities, in particular from clinics, can hence be combined in order to create, on the basis of a large amount of data, a particularly high-quality analysis algorithm using suitable input data. This analysis algorithm can then be provided again in particular to the medical infrastructure facilities that also provided the training data.

A central back-end facility for training also has the advantage that a large processing power dedicated to this purpose can be used there, which also can be used subsequently to perform updates and the like when new training data is available, for instance resulting from cases assessed by the analysis algorithm itself. Of course it is also conceivable in principle, however, to use a processing device of a medical infrastructure facility to perform a training procedure there.

It should also be mentioned in this context that obviously image data available in different coordinate systems is converted into a common coordinate system as part of the present invention, and this obviously also applies to image data for which the patient is in different positions. In other words, it can be provided that registration can be performed between image data acquired in different coordinate systems and/or motion states of the patient. This allows an optimum comparison, to be performed implicitly or explicitly, of features that are visible in images, and the like. In particular in this case, image data from different times are also combined into a common coordinate system. The registration may also include an intensity alignment and/or be based on landmarks, for instance matching anatomical structures and/or lesions.

At least one embodiment of the invention is directed to to an analysis apparatus comprising at least one processor that is designed to perform the method according to at least one embodiment of the invention. All the statements relating to the method according to embodiments of the invention can also be applied analogously to the analysis apparatus according to embodiments of the invention, and therefore the advantages already described can also be achieved by the apparatus.

The analysis apparatus, in at least one embodiment, can comprise for this purpose in particular a training unit, an attribute-data determination unit and an analysis unit. Additional units may be an output unit, a registration unit, various subunits, and the like. The analysis apparatus can comprise a communications interface to an image archiving system (PACS) and/or to an image acquisition apparatus, in particular an image acquisition apparatus used for image monitoring of the intervention, and/or to an information system, for instance a hospital information system (HIS) and/or a radiology information system (RIS), in order to retrieve at least some image data and/or information to be used to determine attribute data or to be used as additional input data.

A computer program according to at least one embodiment of the invention can be loaded directly into a memory of an analysis apparatus, and comprises program segments to perform the steps of at least one embodiment of a method described herein when the computer program is executed in the analysis apparatus.

The computer program can be stored on a non-transitory electronically readable data storage medium according to at least one embodiment of the invention, which therefore comprises electronically readable control information stored thereon that comprises at least one computer program and is designed such that it performs at least one embodiment of a method described herein when the data storage medium is used in an analysis apparatus. The data storage medium may be a non-transient data storage medium, for instance a CD-ROM.

FIG. 1 shows a block diagram for the purpose of explaining an example embodiment of the method according to at least one embodiment of the invention, which in the present case is intended to be used as part of the assessment of the success of a tumor ablation. In this process, X-rays are used as the preliminary image-acquisition modality and as the modality for image monitoring of the minimally invasive intervention, which is performed here using a needle as the instrument. For example, in an intervention space, a radiography apparatus having a C-arm and which may also have a CT-compatible design, can be used as the image acquisition apparatus.

As a preliminary, and not yet shown in detail in FIG. 1, a training process takes place initially, however, in which training data is used to determine input data for an analysis algorithm and to determine the analysis algorithm itself, which is an artificial intelligence algorithm, in this case a random forest algorithm. A deep-learning algorithm is used here, which draws directly on image data contained in the training data. The goal is an analysis algorithm which contains change information about the lesion being treated, in this case a tumor, which information can be used in turn to assess the success of the intervention.

For instance, a degree of reduction in the lesion may be sought as the change information, and/or an attribute change or the like. In the training data, change information of this type, which the analysis algorithm is ultimately meant to determine, is associated with the relevant image data, which in the present case is a pre-intervention image dataset and an intra- and/or post-intervention image dataset, in particular in each case as ground truth. The deep-learning training algorithm identifies the relationships and selects from predetermined attribute data describing attributes of the image data, suitable attribute data as input data of the analysis algorithm, and/or itself defines attributes which can be input to the analysis algorithm as input data via corresponding attribute data.

In addition, intervention information and patient information are also available as training data, which likewise can be used as input data for the analysis algorithm. The training algorithm works out by machine learning the relationships or correlations in the image data and/or in other potential input data relating to the change information, parameterizes the analysis algorithm and defines the input data that this algorithm needs.

It obviously applies here that an update, i.e. further training, can also take place at any time, for which purpose in particular actually assessed interventions can be used for which a guaranteed ground truth exists at a later time. The analysis algorithm can be trained on a back-end facility, which can use training data from various medical infrastructure facilities, for instance clinics.

FIG. 1 now shows the specific use of an analysis algorithm determined in this way for a specific intervention on a patient, so that the success of the intervention can be assessed on the basis of the change information as soon as possible during and/or after the intervention.

In order to determine the input data for the analysis algorithm, two image datasets 1, 2 are assumed also in the specific case, namely a pre-intervention image dataset 1, in this case a CT dataset, which was used for planning and for overlay views during the image-based support of the intervention, and an intra- and/or post-intervention image dataset 2, which here contains as image data X-ray images acquired during and immediately after the intervention and/or three-dimensional X-ray images reconstructed therefrom. An analysis apparatus performing the method can obtain the image datasets 1, 2 here for example from an image archiving system (PACS) connected via a communications interface, directly from an image acquisition apparatus and/or from an information system (HIS/RIS).

The relevant image data from the image datasets 1, 2 is also associated with acquisition parameters, for instance acquisition times, contrast agent properties, X-ray doses, X-ray energy spectra, and the like, which may be relevant to the analysis algorithm and/or to the preceding determination of the attribute data, which will now be described.

In an overall step 3, which, as shown, may contain substeps, the image datasets 1, 2 are analyzed in order to determine the attribute data, which is meant to be used as input data for the analysis algorithm. The overall step 3 may also include a registration step 4, which converts image data acquired in different coordinate systems and/or different motion states of the patient into a common coordinate system.

Further substeps are concerned with different ways of determining attribute data, where obviously the corresponding substeps are needed only when corresponding attribute data is also actually meant to be used in the analysis algorithm.

A substep 5 is concerned with anatomical image analysis. In this substep, identification and position information relating to the lesion and/or the anatomical structures surrounding the lesion is determined automatically using well-known algorithms. Segmentation algorithms, anatomic atlases, and the like can be used here by way of example. In particular in the present case, potential heat sinks that might conduct away the treatment heat are also identified, for instance blood vessels and/or airways in the lungs. Optionally, parameters describing biophysical tissue properties can be determined. It is advantageous in every case to have annotated regions available ultimately.

The substep 6 is concerned with image analysis of the image data that contains the instrument used, in this case a needle as mentioned, in order to determine corresponding identification and position information about this instrument, where again well-known algorithms, for instance segmentation algorithms, can be used. In addition, intervention information 9, which will be discussed in greater detail later, can also already contain geometry information about the medical instrument, which information can be used here (see the corresponding dashed arrow). It should also be mentioned in this context that patient data 8, to be discussed later, can also be taken into account in part in substeps 5 and 6.

Finally, the substep 7 is concerned with determining attribute data relating to more abstract attributes, and determining shape and texture attributes of image data. These relate to different image features, for instance properties of histograms, information relating to the surrounding area of specific image elements, fractal properties, and the like. In this substep 7 is also determined attribute data relating to attributes defined by the training algorithm itself as useful.

It should also be mentioned in this context that this example embodiment also makes use of the particularly advantageous effect of the fact that the image datasets 1 and/or 2 contain spectral-CT data, i.e. multi-energy X-ray data. An even greater number of useful image attributes can be defined and/or derived from such multi-energy X-ray data, for instance separating out contrast agent, and so on. Each item of attribute data also contains, where practical, a time association (acquisition time of the image data from which the attribute data was derived) and a spatial association as classification information, so that therefore within the overall step 3, a form of temporal and/or spatial mapping of the attribute data can take place.

In a step 10, the input data is combined for the analysis algorithm that is to be used in a step 1. The input data comprises the attribute data determined in the overall step 3 and may additionally contain at least elements of the intervention data 9 and of the patient data 8. The intervention data 9 describes the minimally invasive intervention, i.e. can contain information such as intervention times, energy used, measured temperatures, instrument geometry, and the like. Patient data 8 may comprise, for example, blood-clotting attributes, administered medication, and the like.

Once all the input data for the artificial intelligence analysis algorithm is combined, this algorithm is run in a step 11 using this input data, so that the corresponding at least one item of change information 12 is obtained.

The change information 12 may constitute or comprise, for instance, a classification of the intervention result into different classes (residual tumor present, tumor fully removed, and the like), so that in this sense the analysis algorithm can also be considered to be a classifier. Obviously it is also possible that success probabilities, degrees of change, and so on are determined as the change information, which help a user to make the concluding assessment of the intervention success immediately after the intervention.

In addition to presenting the change information 12 itself, it is also provided in this example embodiment to produce an analysis representation, in which important attribute data is presented as an overlay on image data, so that a visual demonstration of the change information can be produced for the user.

If at a later time there is available in association with the minimally invasive intervention looked at here by way of example, a ground truth about the success of the minimally invasive intervention, for instance from an image dataset acquired later, or the like, the corresponding image data can be used, together with additional input data of the analysis algorithm and with the ground truth and, if applicable, divergence information relating to the divergence of the ground truth from the change information that was determined, as additional training data in order to update the analysis algorithm.

Figure 2:
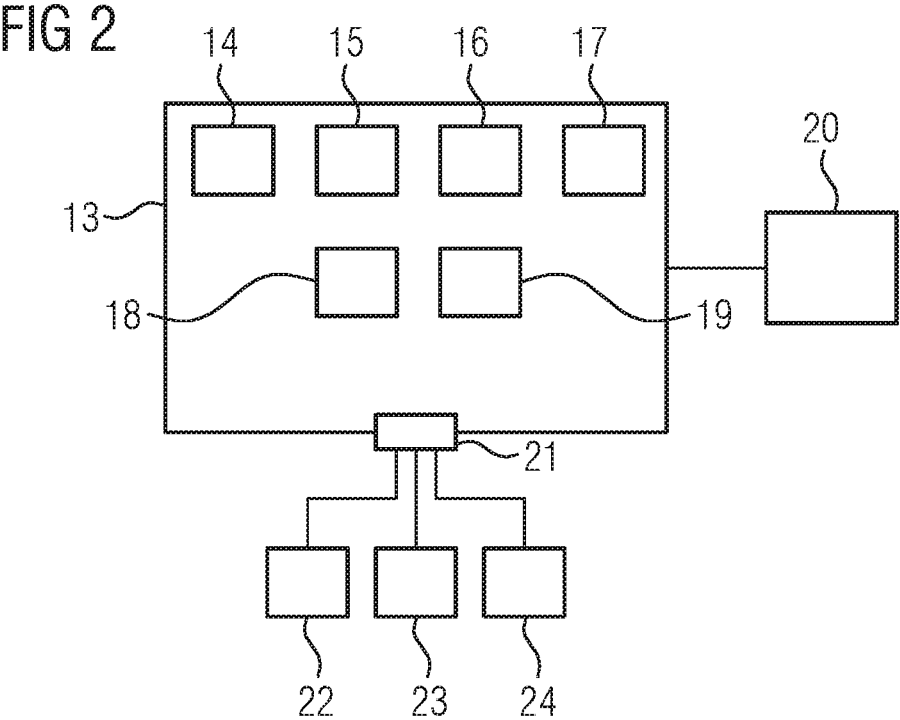
FIG. 2 is a block diagram of an analysis apparatus according to an embodiment of the invention.

FIG. 2 shows a highly abstracted block diagram of an analysis apparatus 13 according to the invention, which can be used to perform the method according to the invention. This apparatus here comprises a training unit 14 for training the analysis algorithm, a registration unit 15 for registering image data, an attribute-data determination unit 16 for performing the overall step 3, an aggregation unit 17 for combining the input data (step 10), an analysis unit 18 for implementing the analysis algorithm, and an output unit 19 for outputting the change information 12, information derived therefrom and/or the analysis representation, for which purpose a suitable output device 20, for example, can be controlled.

There is access via communications interface 21, which the aggregation unit 17, inter alia, can use, to various external data sources, for instance an image archiving system 22, an information system 23 and the memory of an image acquisition apparatus 24.

Although the invention has been illustrated and described in detail using the preferred example embodiment, the invention is not limited by the disclosed examples, and a person skilled in the art can derive other variations therefrom that are still covered by the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method, using image data from a patient after a minimally invasive surgical intervention on a lesion, the method comprising:
    deriving attribute data from a first image dataset and a second image dataset at least in part automatically, the attribute data describing attributes of the image data and being usable as input data to an artificial intelligence analysis algorithm, wherein
        the artificial intelligence analysis algorithm is trained using training data from other patients,
        the training data is associated with a ground truth and a corresponding ground truth image dataset,
        the first image dataset is a pre-intervention image dataset showing the lesion, and
        the second image dataset shows an intervention region at least one of intra-intervention or post-intervention; and
    determining, from the attribute data, change information describing a change in at least one of the lesion or the intervention region as a result of the minimally invasive surgical intervention.

2. The method of claim 1, wherein the artificial intelligence analysis algorithm includes at least one of a neural network or a random forest algorithm.

3. The method of claim 1, wherein at least some of at least one of the attribute data or the attributes are defined by a training algorithm training the artificial intelligence analysis algorithm.

4. The method of claim 1, wherein at least some of the attribute data is selected from a set of candidate data describing candidate attributes.

5. The method of claim 1, wherein
acquisition parameters are at least one of (i) usable as additional input data to the artificial intelligence analysis algorithm or (ii) usable in deriving the attribute data,
the acquisition parameters are associated with at least one of the first image dataset or the second image dataset, and
the acquisition parameters are usable for acquiring at least one of the first image dataset or the second image dataset.

6. The method of claim 5, wherein at least some of the image data includes multi-energy radiographic data containing associated energy-spectrum information.

7. The method of claim 1, wherein the attribute data includes instrument information and at least one of identification information or position information relating to at least one of the lesion or anatomical structures surrounding the lesion, the instrument information relating to an instrument usable and visible in the image data.

8. The method of claim 1, wherein the attribute data includes attribute data describing shape and texture attributes of the image data.

9. The method of claim 1, wherein
at least one of patient information or diagnostic information is at least one of (i) usable as additional input data to the artificial intelligence analysis algorithm or (ii) usable in deriving the attribute data, and
the at least one of the patient information or the diagnostic information relates to at least one of the patient or intervention information describing the minimally invasive surgical intervention.

10. The method of claim 1, wherein classification information allowing at least one of a temporal classification or spatial classification is assigned to each item of at least one of the attribute data or the input data.

11. The method of claim 1, further comprising:
generating an analysis representation to be presented as an overlay on at least some of the image data, the analysis representation being generated from at least one of the change information or at least some of the attribute data, and
outputting the analysis representation.

12. The method of claim 1, further comprising:
using, in response to a ground truth existing for the patient, image datasets from the patient and the ground truth as training data for further training of the artificial intelligence analysis algorithm.

13. An analysis apparatus configured to utilize image data from a patient after a minimally invasive surgical intervention on a lesion, the analysis apparatus comprising:
at least one processor configured to execute computer-readable instructions to cause the analysis apparatus to
derive attribute data from a first image dataset and a second image dataset at least in part automatically, the attribute data describing attributes of image data and being usable as input data to an artificial intelligence analysis algorithm, wherein
the artificial intelligence analysis algorithm is trained using training data from other patients,
the training data is associated with a ground truth and a corresponding ground truth image dataset,
the first image dataset is a pre-intervention image dataset showing the lesion, and
the second image dataset shows an intervention region at least one of intra-intervention or post-intervention, and
determine, from the attribute data, change information describing a change in at least one of the lesion or the intervention region as a result of the minimally invasive surgical intervention.

14. A non-transitory computer-readable storage medium storing program sections, readable and executable by a projection-determining system, to carry out the method of claim 1 when the program sections are executed by the projection-determining system.

15. The method of claim 1, wherein the minimally invasive surgical intervention is tumor ablation on a tumor.

16. The method of claim 3, wherein the training algorithm is a deep-learning algorithm.

17. The method of claim 2, wherein at least some of at least one of the attribute data or the attributes are defined by a training algorithm.

18. The method of claim 2, wherein at least some of the attribute data is selected from a set of candidate data describing candidate attributes.

19. The method of claim 1, further comprising:
using, in response to a ground truth existing for the patient, divergence information between image datasets from the patient and the ground truth as training data for further training of the artificial intelligence analysis algorithm.

20. The analysis apparatus of claim 13, wherein the at least one processor is configured to execute the computer-readable instructions to cause the analysis apparatus to
generate an analysis representation to be presented as an overlay on at least some of the image data, the analysis representation being generated from at least one of the change information or at least some of the attribute data, and
output the analysis representation.

* * * * *